United States Patent
Yamamoto et al.

(10) Patent No.: US 9,625,587 B2
(45) Date of Patent: Apr. 18, 2017

(54) DEVICE FOR READING RADIOLOGICAL IMAGES

(71) Applicant: HAMAMATSU PHOTONICS K.K., Hamamatsu-shi, Shizuoka (JP)

(72) Inventors: Koei Yamamoto, Hamamatsu (JP); Toshihiro Oikawa, Hamamatsu (JP); Hiroki Suzuki, Hamamatsu (JP); Yuichi Miyamoto, Hamamatsu (JP); Naoto Sakurai, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/900,710

(22) PCT Filed: Jun. 10, 2014

(86) PCT No.: PCT/JP2014/065328
§ 371 (c)(1),
(2) Date: Dec. 22, 2015

(87) PCT Pub. No.: WO2014/208328
PCT Pub. Date: Dec. 31, 2014

(65) Prior Publication Data
US 2016/0139278 A1  May 19, 2016

(30) Foreign Application Priority Data
Jun. 25, 2013 (JP) .................................. 2013-132709

(51) Int. Cl.
G01T 1/20 (2006.01)
G03B 42/02 (2006.01)
A61B 6/00 (2006.01)

(52) U.S. Cl.
CPC ............ *G01T 1/2014* (2013.01); *G03B 42/02* (2013.01); *A61B 6/42* (2013.01); *A61B 6/54* (2013.01)

(58) Field of Classification Search
CPC ..................................................... G01T 1/2014
See application file for complete search history.

(56) References Cited

U.S. PATENT DOCUMENTS 6,376,856 B1 * 4/2002 Katagiri ................. G02B 26/10
250/584
2008/0316482 A1 12/2008 Hoshizaki et al.

FOREIGN PATENT DOCUMENTS

CN 102422135 4/2012
JP H06-18415 B2 3/1994
(Continued)

OTHER PUBLICATIONS

International Preliminary Report on Patentability dated Jan. 7, 2016 for PCT/JP2014/065328.

*Primary Examiner* — Marcus Taningco
(74) *Attorney, Agent, or Firm* — Drinker Biddle & Reath LLP (57) ABSTRACT

A radiological image reading device includes a MEMS mirror that scan a recording medium on which a radiological image is recorded with excitation light; a light detecting element that includes a plurality of channels, each channel including a photodiode array, and detects light emitted from an irradiation position of the excitation light on the recording medium; a MEMS mirror driving circuit that determines as a light detection channel to detect the light, a channel corresponding to the irradiation position of the excitation light, out of the plurality of channels; and a reading circuit that reads the detection result of the light from the channel determined by the MEMS mirror driving circuit.

4 Claims, 8 Drawing Sheets

(56) References Cited

FOREIGN PATENT DOCUMENTS

| | | |
|---|---|---|
| JP | H10-210235 A | 8/1998 |
| JP | 2005-104402 | 4/2005 |
| JP | 2005-318151 | 11/2005 |
| JP | 2008-287165 A | 11/2008 |
| JP | 2009-247454 A | 10/2009 |

\* cited by examiner

DEVICE FOR READING RADIOLOGICAL IMAGES

TECHNICAL FIELD

The present invention relates to a radiological image reading device.

BACKGROUND ART

There is a radiological image reading device configured to irradiate a photo-stimulable phosphor sheet including radiological image information with excitation light and detect fluorescence resulting from irradiation with the excitation light (e.g., cf. Patent Literature 1). This radiological image reading device obtains an image signal from the detection result of the fluorescence.

CITATION LIST

Patent Literature

Patent Literature 1: Japanese Unexamined Patent Publication No. S63-176061 (Japanese Examined Patent Publication No. H6-18415).

SUMMARY OF INVENTION

Technical Problem

In the foregoing radiological image reading device, a photodetector detects the fluorescence. A photodiode is conceivably used as the photodetector. When a photodiode with a light receiving region of a small area is used as the photodetector, there is a possibility of loss occurring in the light detection by the photodiode because the fluorescence needs to be condensed onto the light receiving region of the small area. Therefore, the area of the light receiving region of the photodiode is preferably as large as possible. A dark current generated in the photodiode is approximately proportional to the area of the light receiving region. For this reason, increase in the area of the light receiving region could lead to occurrence of the problem of increase in dark current and noise.

An object of the present invention is to provide a radiological image reading device capable of reducing the noise due to the dark current and appropriately detecting luminescence.

Solution to Problem

According to one aspect of the present invention, a radiological image reading device includes light scanning means configured to scan a recording medium on which a radiological image is recorded with excitation light; light detecting means including a plurality of channels, each channel including a photodiode array, and configured to detect light emitted from an irradiation position of the excitation light on the recording medium; controlling means configured to determine as a detection channel to detect the light, a channel corresponding to the irradiation position of the excitation light, out of the plurality of channels; and reading means configured to read the detection result of the light from the detection channel determined by the control means.

In this aspect, the radiological image reading device reads the detection result of the light from the channel (detection channel) corresponding to the irradiation position of the excitation light, so that the light from the recording medium can be suitably detected. Since the radiological image reading device does not read the detection result from channels corresponding to positions away from the irradiation position of the excitation light, the noise due to the dark current is reduced.

In this aspect, the control means may output a first control signal based on the irradiation position of the excitation light to the light scanning means and output a second control signal based on the irradiation position of the excitation light to the reading means. In this case, while a channel according to the second control signal is defined as the detection channel, the reading means reads the detection result from the detection channel. The control means can appropriately make correspondence between the irradiation position of the excitation light and the channel as a reading target (detection channel).

In this aspect, the control means may determine a channel disposed in the vicinity of the irradiation position of the excitation light, as the detection channel. In this case, the radiological image reading device determines the channel close to the irradiation position of the excitation light, as the detection channel, whereby it can detect the light more appropriately.

In this aspect, the photodiode array may include a plurality of avalanche photodiodes operating in Geiger mode; and quenching resistors connected in series to the respective avalanche photodiodes. In this case, the radiological image reading device does not read the detection result from channels corresponding to positions away from the irradiation position of the excitation light, whereby it can minimize influence of noise that increase due to avalanche multiplication. Since the radiological image reading device is configured so as to enhance the sensitivity of the photodiode array by the avalanche multiplication, it can appropriately detect the light from the recording medium even if the light is weak light.

Advantageous Effects of Invention

According to the foregoing aspect of the present invention, the radiological image reading device is provided as one capable of reducing the noise due to the dark current and appropriately detecting luminescence.

BRIEF DESCRIPTION OF DRAWINGS

FIG. 5 shows (a) a cross-sectional view in the direction of arrows II-II of the photodiode array shown in FIG. 4, and (b) a circuit diagram thereof.

DESCRIPTION OF EMBODIMENTS

Embodiments of the present invention will be described below in detail with reference to the accompanying drawings. It is noted that in the description the same elements or elements with the same functionality will be denoted by the same reference signs, without redundant description.

Figure 1:
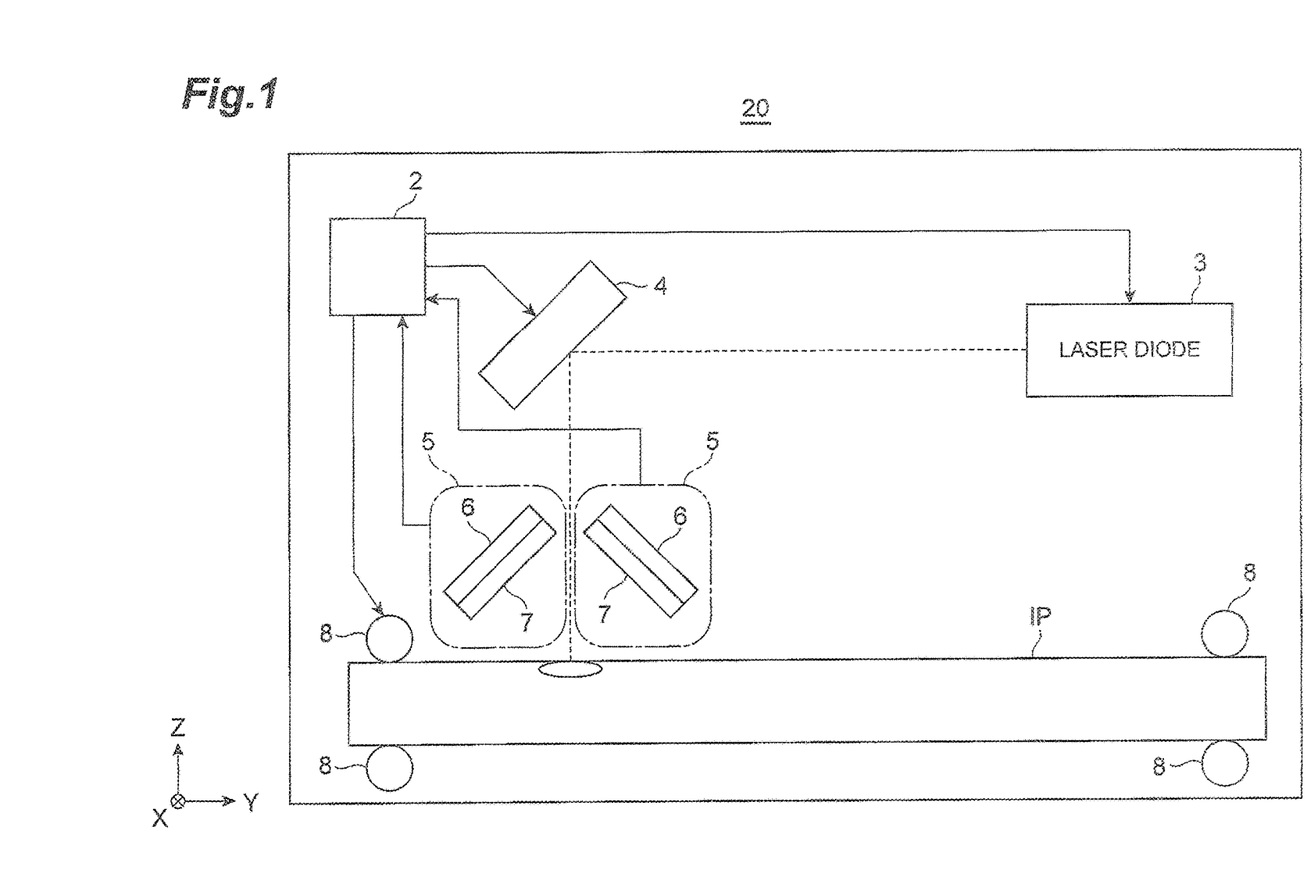
FIG. 1 is a schematic configuration diagram showing a radiological image reading device according to an embodiment.
Figure 2:
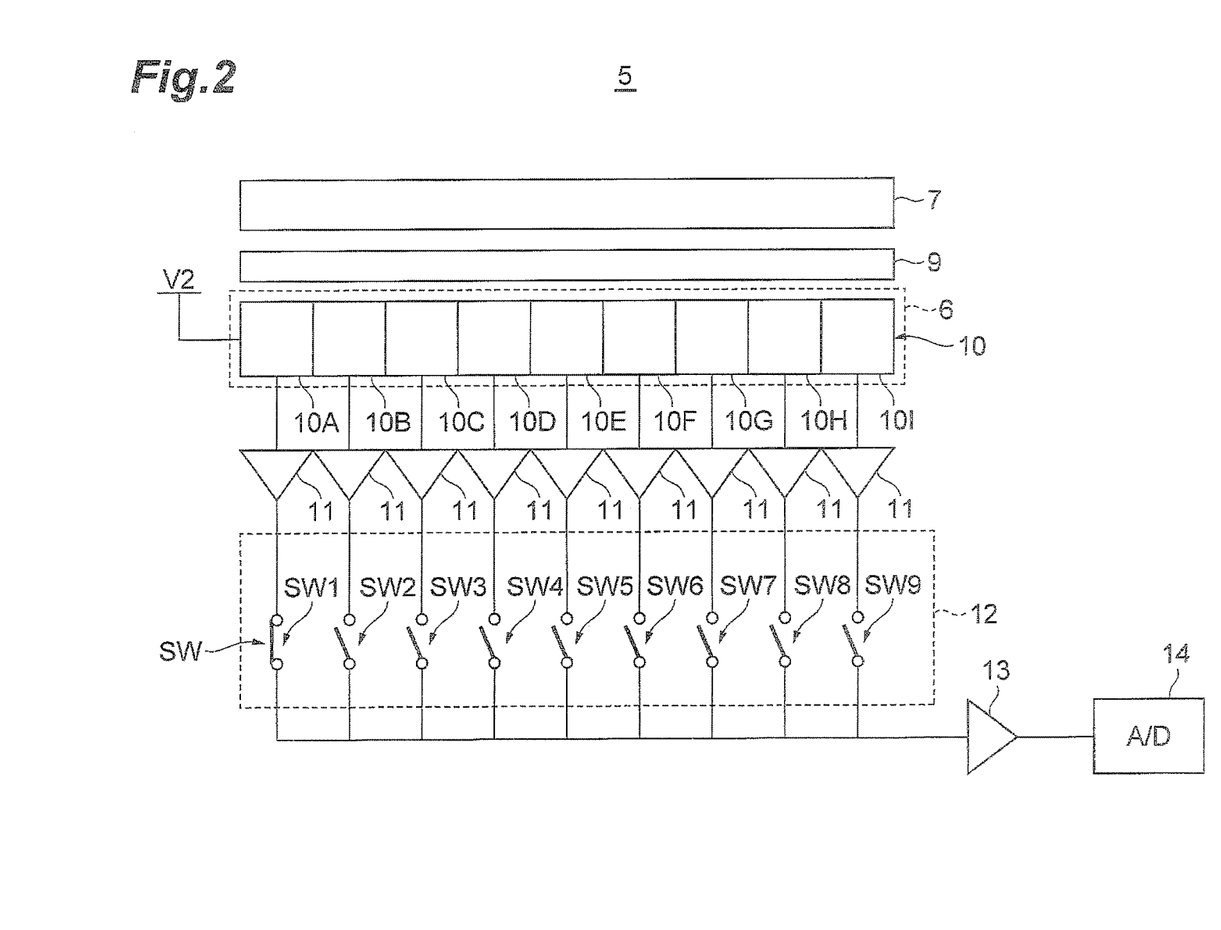
FIG. 2 is a schematic configuration diagram showing a fluorescence detecting unit according to the embodiment.
Figure 3:
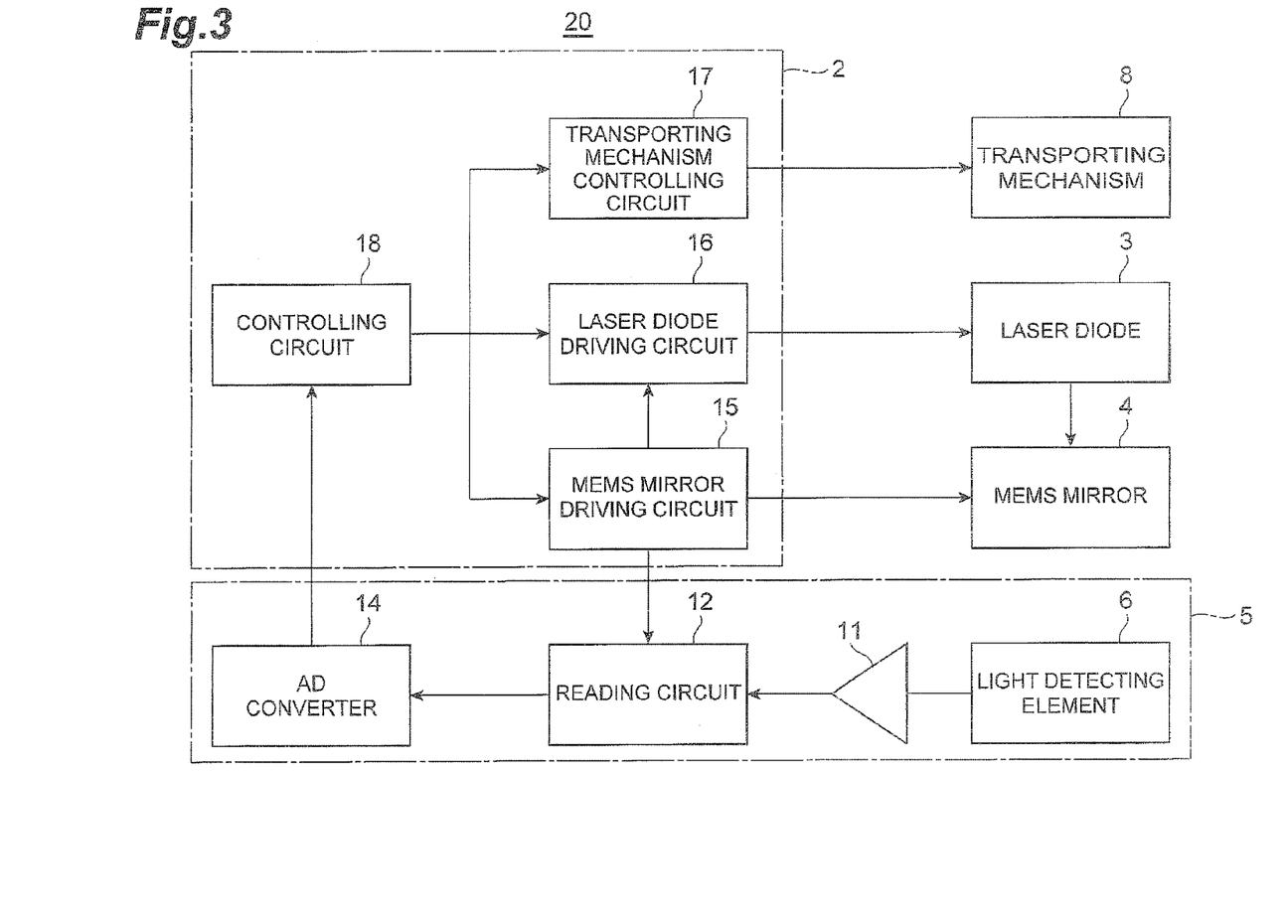
FIG. 3 is a block diagram showing the radiological image reading device according to the embodiment.

First, a radiological image reading device 20 according to the present embodiment will be described with reference to FIGS. 1 to 3. FIG. 1 is a schematic configuration diagram showing the radiological image reading device according to the present embodiment. FIG. 2 is a schematic configuration diagram showing a fluorescence detecting unit according to the present embodiment FIG. 3 is a block diagram showing the radiological image reading device according to the present embodiment.

The radiological image reading device 20 irradiates an imaging plate IP with excitation light and detects light (luminescent light) emitted from the imaging plate IP. The wavelength of the luminescent light (fluorescence) emitted from the imaging plate IP is different from the wavelength of the excitation light. The imaging plate IP is an example of a recording medium on which a radiological image recorded.

The radiological image reading device 20 includes a controlling unit 2 including various controlling circuits. The controlling unit 2 controls the whole radiological image reading device 20. The controlling unit 2 controls operations of a laser diode 3, a MEMS (Micro Electro Mechanical Systems) mirror 4, and a transporting mechanism 8. In the controlling unit 2, a controlling circuit 18 acquires a detection result of the fluorescence from fluorescence detecting units 5. The controlling unit 2, is constituted of hardware of an arithmetic circuit such as CPU (Central Processing Unit), memories such as RAM (Random Access Memory) and ROM (Read Only Memory), a power supplying circuit, a reading circuit including an A/D converter, a driving circuit including a D/A converter, and so on. This controlling unit 2 may be partly or entirely constituted of an integrated circuit such as ASIC (Application Specific Integrated Circuit) or FPGA (Field Programmable Gate Array).

The radiological image reading device 20 includes the transporting mechanism 8 that transports the imaging plate IP along a transportation path extending in a predetermined direction. The transporting mechanism 8 includes a transporting roller and a motor (not shown) that drives the transporting roller.

The radiological image reading device 20 actuates the transporting mechanism 8 to transport the imaging plate IP in the Y-direction in the drawing. The laser diode 3 being a laser light source emits excitation light (laser beam). The emitted excitation light is reflected by the MEMS mirror 4 to being irradiated onto the imaging plate IP. The irradiation of the excitation light onto the imaging plate IP results in emission of fluorescence from the imaging plate IP. The MEMS mirror 4 is an example of an element (light scanning means) that scans the recording medium on which the radiological image recorded with the excitation light.

The MEMS mirror 4 operates in accordance with a control signal from a MEMS mirror driving circuit 15. This operation results in changing inclination of the MEMS mirror 4. In this manner, the MEMS mirror driving circuit 15 outputs the control signal to the MEMS mirror 4 to change the inclination of the MEMS mirror 4, thereby changing a direction of reflection of the excitation light on the MEMS mirror 4. Therefore, it results in changing the irradiation position of the excitation light on the imaging plate IP.

Namely, the radiological image reading device 20 scans the imaging plate IP in the X-direction in the drawing with the excitation light while changing the inclination of the MEMS mirror 4.

The radiological image reading device 20 is provided with two light detecting elements 6. Each of these two light detecting elements 6 detects the fluorescence emitted from the imaging plate IP, through an excitation light removing filter 7. Although the radiological image reading device 20 is provided with the two light detecting elements 6, it may be provided with only one light detecting element 6. The radiological image reading device 20 is provided with the fluorescence detecting units 5. The fluorescence detecting unit 5 includes the light detecting element 6 and excitation light removing filter 7. The fluorescence detecting unit 5 outputs the detection result of the fluorescence.

As shown in FIG. 2, the fluorescence detecting unit 5 is provided with the excitation light removing filter 7, the light detecting element 6 including a plurality of photodiode arrays 10 (nine photodiode arrays 10A to 10I in the present embodiment), a cylindrical lens 9 with a light condensing function, arrayed amplifiers 11 connected to the respective photodiode arrays 10, a reading circuit 12 including switches SW (nine switches SW1 to SW9 in the present embodiment) connected to the respective amplifiers 11, an amplifier 13, and an AD converter 14.

The light detecting element 6 includes a plurality of channels, each channel including a photodiode array 10. The below will describe the configuration of the photodiode array 10 according to the present embodiment, with reference to FIGS. 4 to 6. The light detecting element 6 is an example of an element (light detecting means) that detects light emitted from the irradiation position of the excitation light on the recording medium.

Figure 4:
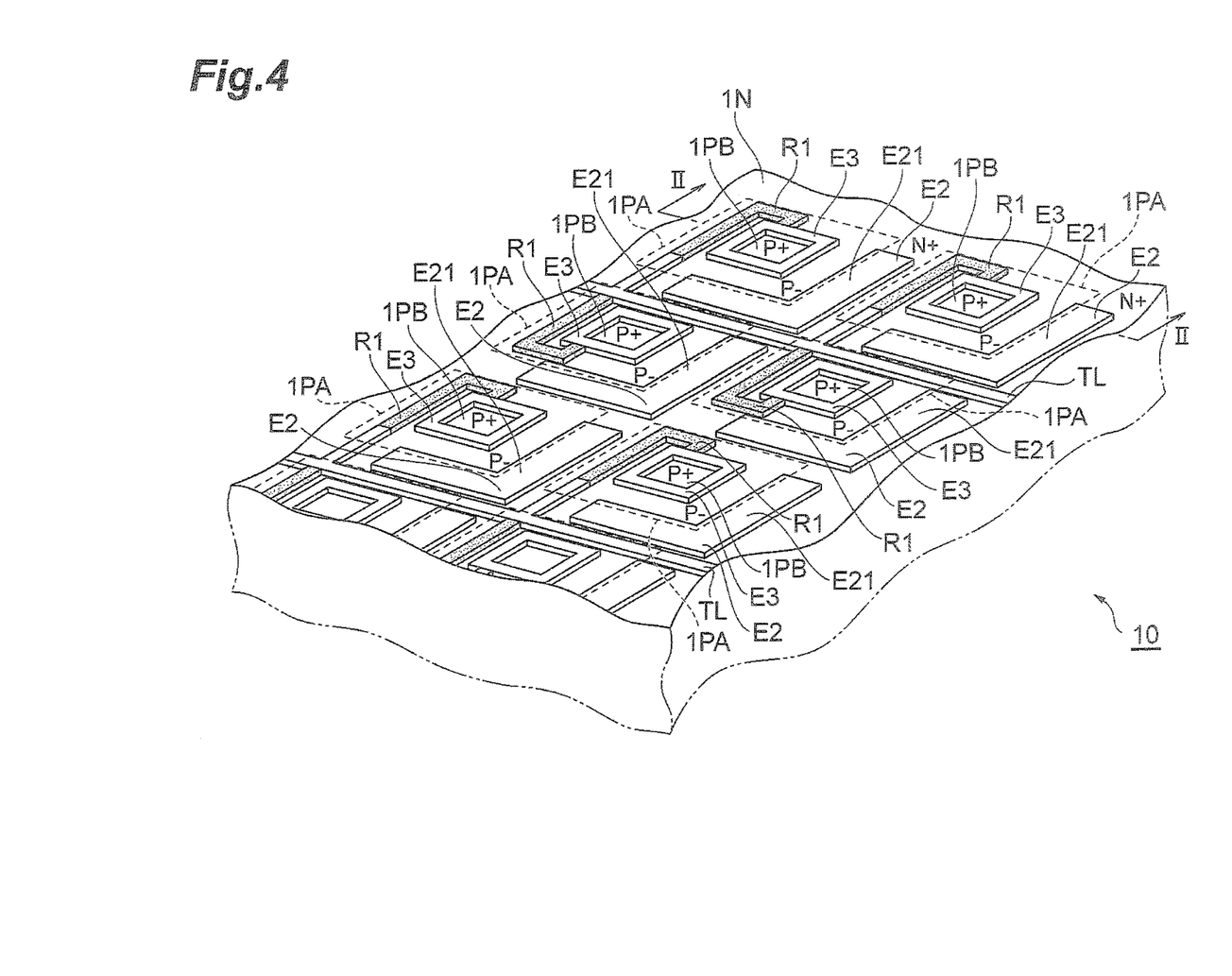
FIG. 4 is a perspective view of a photodiode array according to the embodiment.
Figure 5:
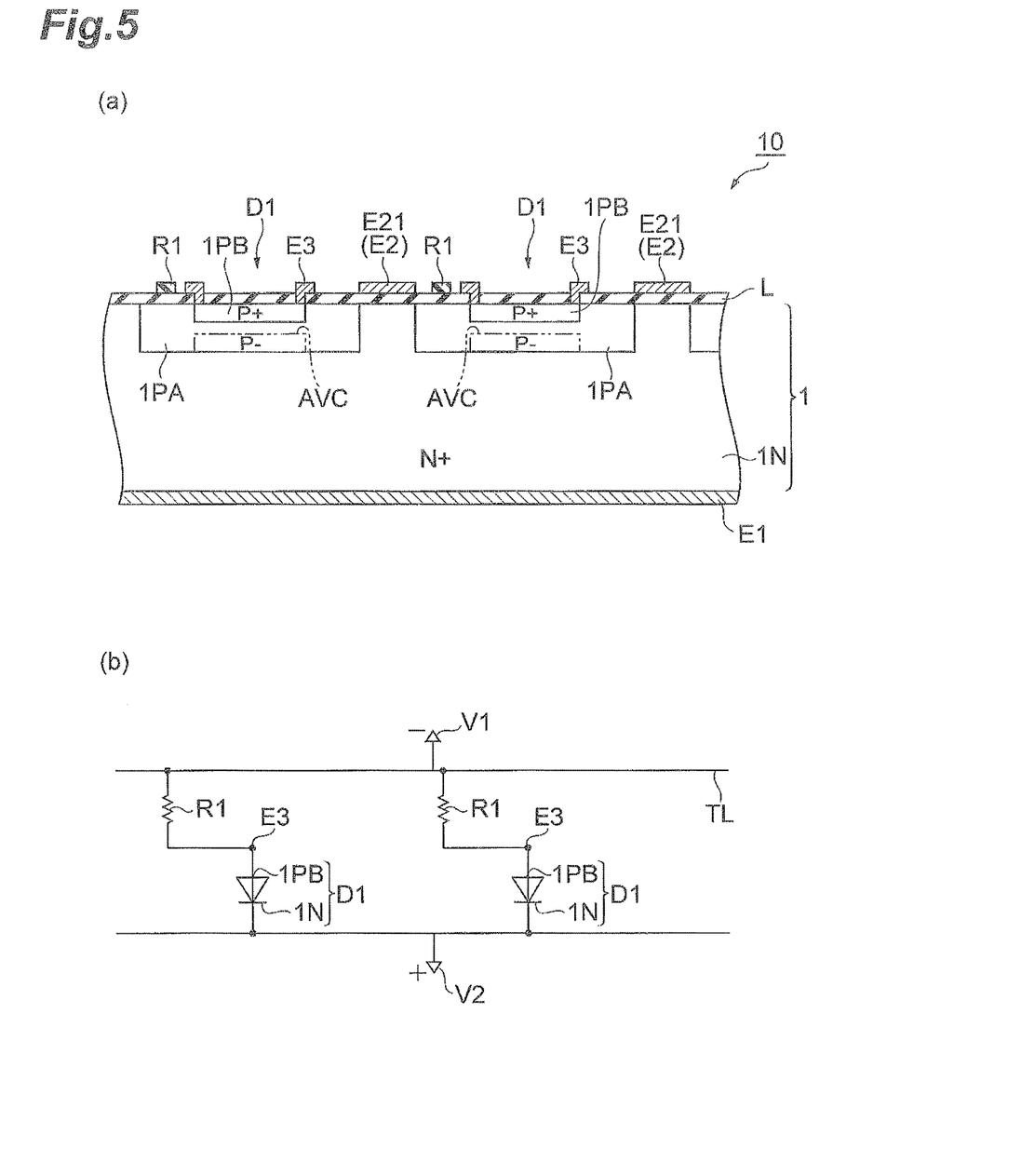
Figure 6:
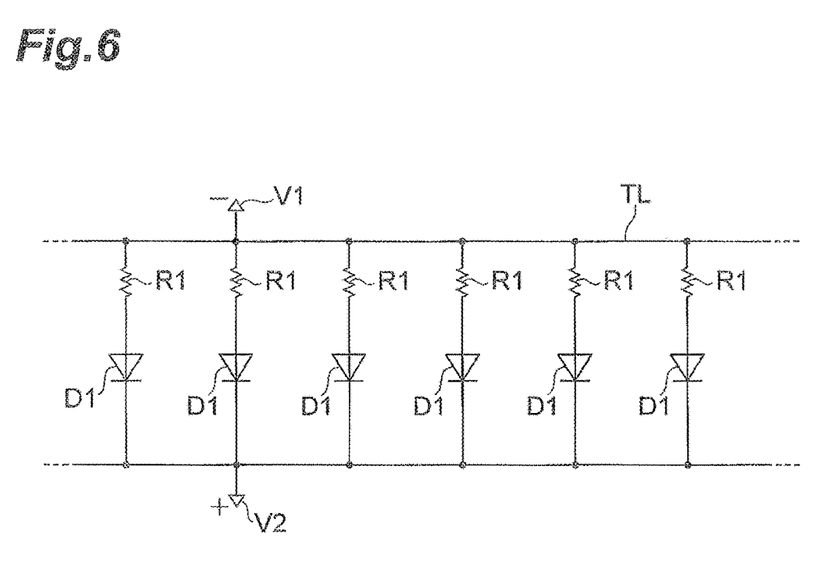
FIG. 6 is an overall circuit diagram of the photodiode array according to the embodiment.

FIG. 4 is a perspective view of the photodiode array according to the embodiment. FIG. 5 shows (a) a cross-sectional view in the direction of arrows II-II of the photodiode array shown in FIG. 4, and (b) a circuit diagram thereof. FIG. 6 is an overall circuit diagram of the photodiode array according to the embodiment.

In the photodiode array 10, a plurality of photodiodes D1 (cf. FIG. 6) are formed on an N-type (first conductivity type) semiconductor substrate 1N.

Each individual photodiode D1 includes a P-type (second conductivity type) first semiconductor region 1PA formed on one surface side of the semiconductor substrate 1N, and a P-type (second conductivity type) second semiconductor region 1PB formed in the first semiconductor region 1PA. The second semiconductor region 1PB has a higher impurity concentration than the first semiconductor region 1PA. The photodiode D1 includes a first electrode E1 electrically connected to the semiconductor substrate 1N and a surface electrode E3 formed on the second semiconductor region 1PB. The planar shape of the first semiconductor region 1PA is quadrangular. The second semiconductor region 1PB is located inside the first semiconductor region and the planar shape thereof is quadrangular. The depth of the first semiconductor region 1PA is larger than that of the second semiconductor region 1PB. The semiconductor substrate 1 in FIG. 5 indicates that including both of the N-type semiconductor substrate 1N and the P-type semiconductor regions 1PA, 1PB.

The photodiode array 10 includes a first reflector E2 constituting a metal layer, and a resistive layer (quenching resistor) R1, for each of the individual photodiodes D1. The first reflector E2 is formed through an insulating layer L (cf. FIG. 5) on the semiconductor substrate 1N outside the first semiconductor region 1PA. The resistive layer R1 includes one end continuous to the surface electrode E3 and extends along the surface of the insulating layer L on the first semiconductor region 1PA. In FIG. 4, illustration of the insulating layer L shown in FIG. 5 is omitted for clarity of structure.

The first reflector E2 includes a reflector E21 constituting a metal layer with the planar shape of an L-shape. The reflector E21 (first reflector E2) located on the semiconductor region 1N is electrically isolated from the surface electrode E3 of a ring shape having a first opening. Namely, an anode and a cathode of the photodiode D1 are provided with respective electrodes and one surface electrode E3 is electrically separated from the first reflector E2. This makes the first reflector E2 definitely distinguished from the surface electrode E3 and increases degrees of freedom for design to arrange it at a location suitable for reflection. The other end of the resistive layer R1 connected to each individual photodiode D1 is electrically connected, through a wiring electrode continuous to the resistive layer R1 if necessary, to a common signal readout line TL.

In FIG. 4, a pair of photodiodes (regions immediately below the semiconductor regions 1PA) adjacent in a column direction are connected though their respective resistive layers R1 to the signal readout line TL extending in a row direction. A plurality of pairs of photodiodes are connected through their respective resistive layers R1 to one signal readout line TL. A plurality of signal readout lines TL extending in the row direction are arranged along the column direction. A plurality of pairs of photodiodes are also connected similarly through their respective resistive layers R1 to each of the individual signal readout lines TL. All the signal readout lines TL shown in FIG. 4 are connected eventually to constitute the circuit as shown in FIG. 6, as one signal readout line TL in terms of circuitry.

The resistive layer R1 has the higher resistivity than the surface electrode E3 to which it is connected, and has the higher resistivity than the first reflector E2. Specifically, the resistive layer R1 is made of polysilicon and the rest electrodes and reflector all are made of metal such as aluminum. When the semiconductor substrate 1 is made of Si, an electrode material often used is AuGe/Ni or the like, besides aluminum. In the case using Si, a P-type impurity includes a Group 3 element such as B and an N-type impurity includes a Group 5 element such as N, P, or As. A device may be configured by replacing the N-type and P-type of conductivity types of semiconductors with each other, while the device can also function well. Examples of methods for adding these impurities include the diffusion method, and ion implantation method.

Examples of materials for the insulating layer L include $SiO_2$ and SiN. When the insulating layer L is made, for example, of $SiO_2$, examples of methods for forming the insulating layer L include the thermal oxidation method and the sputtering method.

In the case of the above-described structure, a PN junction is constituted between the N-type semiconductor substrate 1N and the P-type first semiconductor region 1PA, thereby forming the photodiode D1. The semiconductor substrate 1N is electrically connected to the first electrode E1 that is formed on the back surface of the substrate. The first semiconductor region 1PA is connected through the second semiconductor region 1PB to the surface electrode E3. The resistive layer R1 is connected in series to the photodiode D1 (cf. (b) of FIG. 5).

In the photodiode array 10, each individual photodiode D1 operates in Geiger mode. In Geiger mode, a reverse voltage (reverse bias voltage) larger than the breakdown voltage of the photodiode D1 is applied between the anode and cathode of the photodiode D1. Namely, a (−) potential V1 is applied to the anode and a (+) potential V2 to the cathode. The polarities of these potentials are relative ones, and it is also possible to set one of the potentials to the ground potential.

The anode includes the P-type semiconductor region 1PA and the cathode includes the N-type semiconductor substrate 1N. The photodiode D1 functions as an avalanche photodiode. When light (photons) is incident to the photodiode D1, photoelectric conversion takes place inside the substrate to generate photoelectrons. In a neighboring region AVC near the PN junction interface in the first semiconductor region 1PA shown in (a) of FIG. 5, avalanche multiplication is induced and a group of multiplied electrons flow toward the electrode E1.

The first reflector E2 is disposed on the surface of the semiconductor substrate 1N outside the first semiconductor region 1PA with the relatively low impurity concentration, compared to the second semiconductor region 1PB. The region of exposed surface of the semiconductor substrate 1N includes a dead space having little contribution to detection, for incidence of light. The first reflector E2 reflects incident light and makes the reflected light incident to a second reflector (e.g., an inner surface of a metal package or the like). The second reflector again reflects the incident light to effectively guide the re-reflected light to the photodiodes D1.

The other ends of the resistive layers R1 connected to the individual photodiodes D1 are electrically connected to the common signal readout line TL along the surface of the semiconductor substrate 1N. The plurality of photodiodes D1 operate in Geiger mode and each photodiode D1 is connected to the common signal readout line TL. For this reason, when photons are simultaneously incident to the plurality of photodiodes D1, outputs from the plurality of photodiodes D1 are fed all to the common signal readout line TL and are measured as a high-intensity signal according to the number of incident photons as a whole. A load resistor to cause a voltage drop for readout of signal may be connected to the signal readout line TL.

The above-described configuration is the configuration of the front-illuminated photodiode array, and it is also possible to adopt the configuration of the back-illuminated photodiode array. In this case, the thickness of the semiconductor substrate 1N is made smaller and the backside electrode E1 is made as a transparent electrode. The back-side electrode E1 may be located at another position (e.g., on the front surface side of the substrate) on the semiconductor substrate 1N.

Reference is made again to FIG. 2. The cylindrical lens 9 condenses the fluorescence emitted from the imaging plate IP. The cylindrical lens 9 may be replaced with a micro lens array as an element that condenses the fluorescence. The output of the detection result by each light detecting element 6 is amplified by the amplifier 11 and then read by the reading circuit 12. The output from the reading circuit 12 is subjected to A/D conversion in the AD converter 14. The reading circuit 12 includes a multiplexer. The reading circuit 12 is an example of an element (reading means) that reads the detection result from the detection channel to detect light.

As shown in FIG. 3, the radiological image reading device 20 is provided with the light detecting element 6, laser diode 3, MEMS mirror 4, array of amplifiers 11, reading circuit 12, AD converter 14, MEMS mirror driving circuit 15, controlling circuit 18, laser diode driving circuit 16, transporting mechanism controlling circuit 17, and transporting mechanism 8.

The controlling unit 2 includes the controlling circuit 18, transporting mechanism controlling circuit 17, laser diode driving circuit 16, and MEMS mirror driving circuit 15. The controlling circuit 18 acquires the output of the detection result by the light detecting element 6 after the A/D conversion from the AD converter 14. The controlling circuit 18 controls the transporting mechanism controlling circuit 17, laser diode driving circuit 16, and MEMS mirror driving circuit 15.

The transporting mechanism controlling circuit 17 actuates the transporting mechanism 8 to transport the imaging plate IP in the Y-direction as shown in FIG. 1. The laser diode driving circuit 16 outputs a control signal to the laser diode 3 to make the laser diode 3 emit the excitation light.

The MEMS mirror driving circuit 15 outputs a control signal as a first control signal to the MEMS mirror 4 to control the inclination of the MEMS mirror 4. Specifically, the MEMS mirror driving circuit 15 determines the inclination of the MEMS mirror 4 and outputs the control signal based on the inclination to the MEMS mirror 4 to control the inclination of the MEMS mirror 4. The MEMS mirror driving circuit 15 is an example of an element (control means) that determines a detection channel.

The MEMS mirror driving circuit 15 outputs a control signal corresponding to the first control signal, as a second control signal to the reading circuit 12. The reading circuit 12 turns on the switch SW corresponding to the photodiode array 10 as a reading target, based on the second control signal. Namely, the MEMS mirror driving circuit 15 determines the photodiode array 10 of the reading target out of the plurality of photodiode arrays 10, as a detection channel.

The first control signal output to the MEMS mirror 4 by the MEMS mirror driving circuit 15 corresponds to the inclination of the MEMS mirror 4. Therefore, the position irradiated with the excitation light reflected by the MEMS mirror 4 on the imaging plate IP is specified by the first control signal, or the second control signal.

The MEMS mirror driving circuit 15 outputs the second control signal corresponding to the first control signal output to the MEMS mirror 4, to the reading circuit 12 to make the reading circuit 12 operate based on the second control signal. This causes the radiological image reading device 20 to obtain the detection result of the fluorescence from the photodiode array 10 corresponding to the irradiation position of the excitation light on the imaging plate IP.

When the MEMS mirror driving circuit 15 outputs the first control signal to the MEMS mirror 4, the MEMS mirror 4 becomes inclined according to the first control signal. As a result, the excitation light output from the laser diode 3 is reflected by the MEMS mirror 4 to being irradiated onto the imaging plate IP.

The MEMS mirror driving circuit 15 outputs the second control signal corresponding to the inclination of the MEMS mirror 4 (i.e., the second control signal corresponding to the position irradiated with the excitation light on the imaging plate IP) to the reading circuit 12 to make the switch SW in the reading circuit 12 operate, based on the second control signal. For example, the MEMS mirror driving circuit 15 turns on the switch SW corresponding to the photodiode array 10 closest to the irradiation position of the excitation light. The MEMS mirror driving circuit 15 determines the photodiode array 10 closest to the irradiation position of the excitation light, as a reading target on the imaging plate IP and outputs the second control signal corresponding to the inclination of the MEMS mirror 4 to the reading circuit 12.

Figure 7:
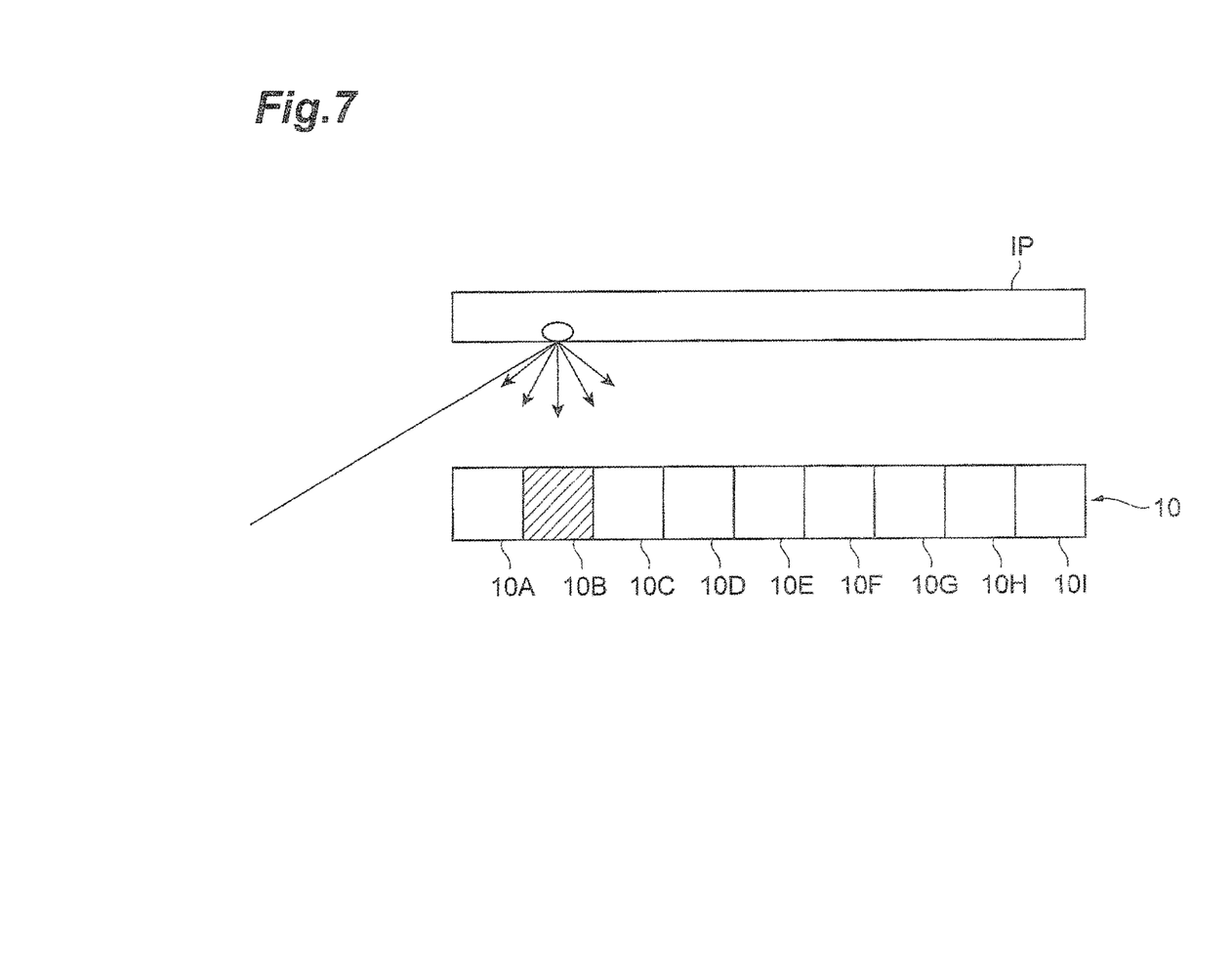
FIG. 7 is a drawing for illustrating a reading operation in a reading circuit.

For example, as shown in FIG. 7, when the radiological image reading device 20 irradiates the imaging plate IP with the excitation light, the MEMS mirror driving circuit 15 outputs the second control signal to the reading circuit 12, the second control signal corresponding to the first control signal output to the MEMS mirror 4. As a result of this, the reading circuit 12 turns on the switch SW2 corresponding to the photodiode array 10B at the closest position to the irradiation position of the excitation light, in the light detecting element 6. FIG. 7 is a drawing for illustrating the reading operation in the reading circuit.

The MEMS mirror driving circuit 15 outputs to the reading circuit 12, the second control signal corresponding to the first control signal output to the MEMS mirror 4. This allows the circuit to appropriately make correspondence between the irradiation position of the excitation light and the photodiode array 10 as a reading target. The reading circuit 12 turns on the switch SW (the switch SW2 in the example shown in FIG. 7) corresponding to the photodiode array 10 closest to the irradiation position of the excitation light (the photodiode array 10B in the example shown in FIG. 7). The radiological image reading device 20 reads only the detection result by the photodiode array 10 closest to the irradiation position of the excitation light. Therefore, the radiological image reading device 20 can read the detection result of the light detecting element 6 more appropriately.

The MEMS mirror driving circuit 15 may output another control signal that can specify the inclination of the MEMS mirror 4 or the irradiation position of the excitation light as the second control signal, instead of outputting the second control signal corresponding to the first control signal output to the MEMS mirror 4, to the reading circuit 12. In this case as well, the MEMS mirror driving circuit 15 outputs to the reading circuit 12 the control signal that can specify the inclination of the MEMS mirror 4 or the irradiation position of the excitation light, whereby the radiological image reading device 20 can appropriately make the correspondence between the irradiation position of the excitation light and the photodiode array 10 of the reading target.

Figure 8:
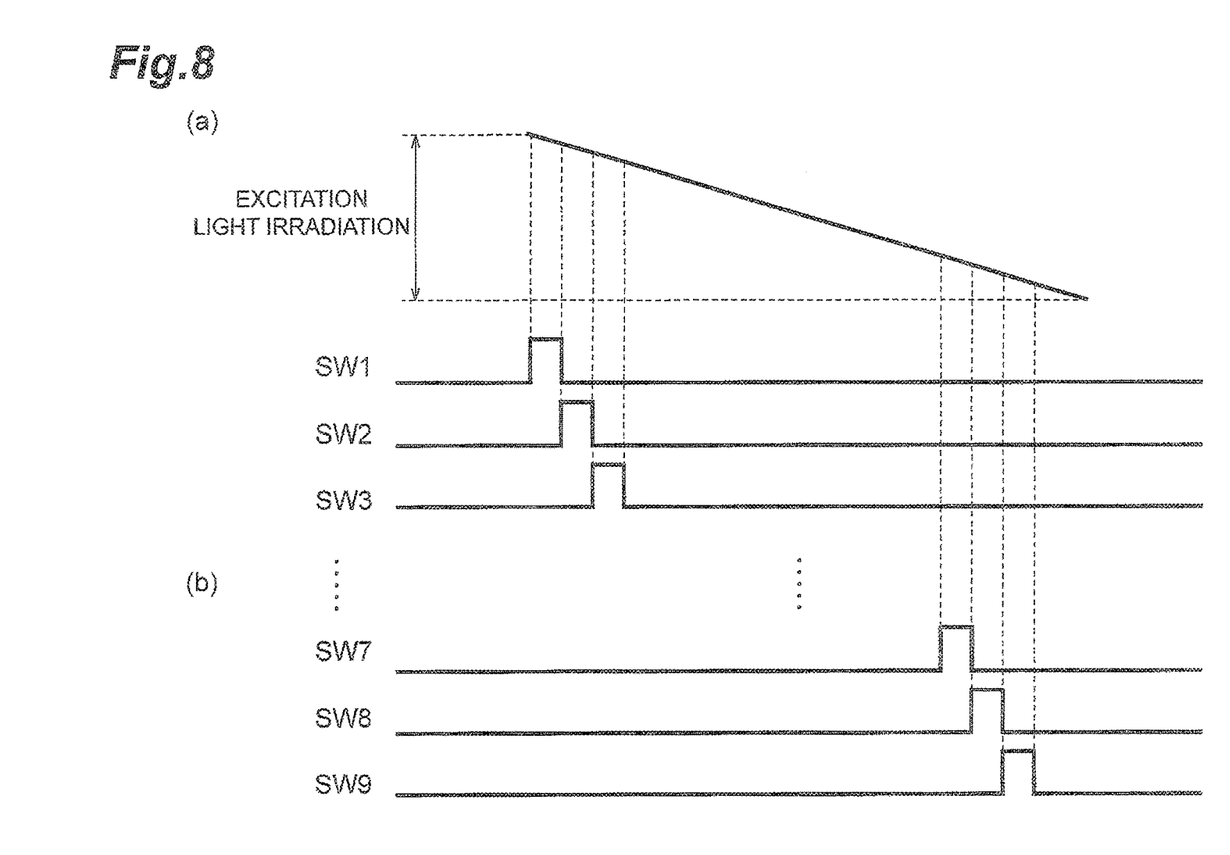
FIG. 8 is a diagram showing first and second control signals.

The following will describe the relationship between scanning position and operation of the reading circuit, with reference to FIG. 8. FIG. 8 is a drawing for illustrating the relationship between scanning position and operation of the reading circuit. The MEMS mirror driving circuit 15 outputs the first control signal as shown in (a) in FIG. 8 to the MEMS mirror 4, so as to irradiate with the excitation light from the photodiode array 10A side to the photodiode array 10I side on the imaging plate IP. Then the MEMS mirror driving circuit 15 outputs the corresponding second control signal to the reading circuit 12.

In this case, as shown in (b) in FIG. 8, the reading circuit 12 operates so as to turn on the switch SW corresponding to the photodiode array 10 closest to the irradiation position of the excitation light, in accordance with the second control signal output by the MEMS mirror driving circuit 15. Namely, the reading circuit 12 operates to turn on the switch SW corresponding to the photodiode array 10 closest to the irradiation position of the excitation light.

This causes the radiological image reading device 20 to acquire only the detection result of the photodiode array 10 closest to the irradiation position of the excitation light. Therefore, the radiological image reading device 20 can appropriately detect the luminescent light. The radiological image reading device 20 does not read the detection result from the photodiode arrays 10 corresponding to positions away from the irradiation position of the excitation light. Therefore, the noise due to the dark current is reduced.

The radiological image reading device 20 reads only the detection result of the photodiode array 10 located in the vicinity of the irradiation position of the excitation light. Therefore, it can read the detection result of the light detecting element 6 more appropriately.

The radiological image reading device 20 reads only the detection result of the photodiode array 10 closest to the irradiation position of the excitation light, but the device does not have to be limited only to this. For example, the radiological image reading device 20 may also read the detection result of the photodiode array 10 located around the photodiode array 10 closest to the irradiation position of the excitation light, as the photodiode array 10 corresponding to the irradiation position of the excitation light.

The photodiode array 10 includes the plurality of avalanche photodiodes that operate in Geiger mode (photodiodes D1) and the quenching resistors (resistive layers R1) connected in series to the respective avalanche photodiodes. Since the radiological image reading device 20 does not read the detection result from the photodiode arrays 10 corresponding to positions away from the irradiation position of the excitation light, it can minimize influence of noise that increase due to avalanche multiplication. Since the radiological image reading device 20 is configured to enhance the sensitivity of the photodiode array 10 by avalanche multiplication, it can appropriately detect the fluorescence from the imaging plate IP even if the fluorescence is weak light.

The embodiment of the present invention has been described above, but it should be noted that the present invention is not always limited only to the foregoing embodiment but can be modified in many ways without departing from the spirit and scope of the invention.

INDUSTRIAL APPLICABILITY

The present invention is applicable to the radiological image reading device that detects the fluorescence light emitted from the recording medium on which the radiological image is recorded.

REFERENCE SIGNS LIST 1 semiconductor substrate; 2 controlling unit; 3 laser diode; 4 MEMS mirror; 5 fluorescence detecting unit; 6 light detecting element; 10 photodiode array; 12 reading circuit; 15 MEMS mirror driving circuit; 16 laser diode driving circuit; 18 controlling circuit; 20 radiological image reading device; IP imaging plate.

The invention claimed is:

1. A radiological image reading device comprising:
light scanning means configured to scan a recording medium on which a radiological image is recorded with excitation light;
light detecting means including a plurality of channels, each channel including a photodiode array, and configured to detect light emitted from an irradiation position of the excitation light on the recording medium;
a plurality of first amplifiers connected to the respective photodiode arrays, each first amplifier amplifying an output from the corresponding photodiode array;
controlling means configured to determine as a detection channel to detect the light, a channel corresponding to the irradiation position of the excitation light, out of the plurality of channels;
reading means connected to the plurality of first amplifiers and configured to read an output from the first amplifier to which the photodiode array included in the detection channel determined by the control means is connected; and
a second amplifier connected to the reading means and amplifying an output from the reading means.

2. The radiological image reading device according to claim 1,
wherein the controlling means outputs a first control signal based on the irradiation position of the excitation light to the light scanning means and outputs a second control signal based on the irradiation position of the excitation light to the reading means.

3. The radiological image reading device according to claim 1,
wherein the controlling means determines a channel disposed in the vicinity of the irradiation position of the excitation light, as the detection channel.

4. The radiological image reading device according to claim 1,
wherein the photodiode array has a plurality of avalanche photodiodes operating in Geiger mode; and quenching resistors connected in series to the respective avalanche photodiodes.

* * * * *